United States Patent
Soto

(10) Patent No.: US 7,496,971 B2
(45) Date of Patent: Mar. 3, 2009

(54) MASSAGE DRAPE

(75) Inventor: Daniel A. Soto, 77 Ogden St., Springfield, MA (US) 01151

(73) Assignee: Daniel A. Soto, Springfield, MA (US)

( * ) Notice: Subject to any disclaimer, the term of this patent is extended or adjusted under 35 U.S.C. 154(b) by 317 days.

(21) Appl. No.: 11/153,158

(22) Filed: Jun. 15, 2005

(65) Prior Publication Data

US 2005/0284488 A1 Dec. 29, 2005

Related U.S. Application Data

(60) Provisional application No. 60/579,598, filed on Jun. 15, 2004.

(51) Int. Cl.
A41D 10/00 (2006.01)
(52) U.S. Cl. .......................................... 2/114
(58) Field of Classification Search .................. 2/69, 2/69.5, 114, 88, 111, 908; 5/413 R, 482; 128/849
See application file for complete search history.

(56) References Cited

U.S. PATENT DOCUMENTS

| | | | | |
|---|---|---|---|---|
| 906,551 A * | 12/1908 | Newman | ...................... | 2/69.5 |
| 1,496,283 A * | 6/1924 | Wright | ............................. | 2/88 |
| 2,227,751 A * | 1/1941 | Idelman | ......................... | 2/69.5 |
| 2,268,317 A * | 12/1941 | Till | ................................ | 2/89 |
| 2,442,105 A * | 5/1948 | Vacheron | ...................... | 2/69.5 |
| 2,656,540 A * | 10/1953 | Stephenson | .................... | 2/69.5 |
| 3,030,957 A * | 4/1962 | Melges | ........................ | 604/357 |
| 3,034,132 A * | 5/1962 | Landsberger et al. | ......... | 2/69.5 |
| 3,079,611 A * | 3/1963 | Boryszewski | .................... | 2/89 |
| 3,251,360 A * | 5/1966 | Melges | ........................ | 128/853 |
| 3,483,575 A * | 12/1969 | McCarthy | .................. | 5/413 R |
| 3,745,587 A * | 7/1973 | Bradley | ......................... | 2/114 |
| 4,142,264 A * | 3/1979 | Whiting | ......................... | 5/482 |
| 4,217,662 A * | 8/1980 | Buchman | ...................... | 2/69.5 |
| 4,258,439 A * | 3/1981 | York | ............................. | 2/69.5 |
| 4,484,362 A * | 11/1984 | Asher | ............................. | 2/69 |
| 4,587,682 A * | 5/1986 | Schultz | ...................... | 5/413 R |
| 4,669,128 A * | 6/1987 | Furgang | ......................... | 2/69 |
| 4,674,130 A * | 6/1987 | Coudron | ...................... | 2/69.5 |
| 4,688,282 A * | 8/1987 | Jeffries | ...................... | 5/413 R |
| 4,752,971 A * | 6/1988 | Meserol | ........................ | 2/88 |
| 5,012,543 A * | 5/1991 | Lewis, Sr. | .................. | 15/209.1 |
| 5,243,724 A * | 9/1993 | Barnes | ......................... | 5/482 |
| 5,274,852 A * | 1/1994 | Hogan | ........................... | 2/114 |
| 5,887,299 A * | 3/1999 | Phillips | ...................... | 5/413 R |
| 5,887,301 A * | 3/1999 | Anderson | ...................... | 5/482 |

(Continued)

FOREIGN PATENT DOCUMENTS

DE 29508098 U1 * 9/1996

(Continued)

Primary Examiner—Alissa L Hoey
(74) Attorney, Agent, or Firm—McCormick, Paulding & Huber LLP

(57) ABSTRACT

A massage drape for modesty and warmth and a storage system therefore. The massage drape includes an upper and lower portion, which are secured together via fasteners forming a two-ply drape. The drape also includes fasteners that allow the drape to be placed on a user's body in several configurations. Moreover, the drape eliminates the procedure of lifting and rotating a sheet once a user gets on a massage table.

7 Claims, 4 Drawing Sheets

U.S. PATENT DOCUMENTS

| | | | |
|---|---|---|---|
| 6,175,964 B1 * | 1/2001 | Adler | 2/207 |
| 6,199,232 B1 * | 3/2001 | Kocivar | 5/502 |
| 6,341,397 B1 * | 1/2002 | Kliegl et al. | 5/482 |
| 6,578,204 B2 * | 6/2003 | Ozenkoski | 2/86 |
| 2005/0044606 A1 * | 3/2005 | Flanagan-Frazier | 2/69 |
| 2005/0102727 A1 * | 5/2005 | Kelly | 2/69 |

FOREIGN PATENT DOCUMENTS

ZA    200508114 A  *  7/2006

* cited by examiner

MASSAGE DRAPE

CROSS-REFERENCE TO RELATED APPLICATIONS

The present application claims priority to Provisional Patent Application No. 60/579,598 filed on Jun. 15, 2004, hereby incorporated by reference in its entirety.

FIELD OF THE INVENTION

The present invention relates generally to massage equipment and more specifically to a multi-function massage drape.

BACKGROUND OF THE INVENTION

Typically, professional massages are performed on a massage table, which includes a portion that supports a person's body. A person receiving a professional massage must first disrobe before getting onto the table to receive the massage. Generally, the person will disrobe and place a sheet, typically a twin sheet, around his or her body for modesty and warmth. This sheet also selectively covers portions of a person's body when he or she is on the table. When a person initially gets on the massage table, the sheet is typically positioned to cover the person's entire body. To accomplish this, the entire sheet is lifted and rotated 90 degrees so that the rectangular sheet's longer dimension is parallel to the plane of the person's body. The sheet may then be adjusted to reveal portions of the person's body to be massaged. This sheet is often referred to as a drape sheet or massage drape.

Most people use conventional twin sheets as massage drapes to cover themselves before and during a professional massage. Such sheets, however, are quite thin and provide little protection from nudity and insufficient warmth. They are also difficult to secure to a person's body, especially for women who must cover their breasts. It is also difficult to transition between standing with the sheet and laying face down on the table with the sheet positioned to cover the user's back. Moreover, such sheets are difficult to lengthen and shorten when a person is on the massage table as they must be lifted and rotated.

In light of the above, a need exists for massage drape that offers complete protection from nudity and provides sufficient warmth. Additionally, a need exists for a massage drape that may be easily and securely attached to a person's body and may be easily shortened and lengthened once the person is on the massage table. The present invention fulfills these needs and more.

SUMMARY OF THE INVENTION

It is an object of the present invention to provide a massage drape that offers complete protection from nudity.

It is an additional object of the present invention to provide a massage drape that provides sufficient warmth.

It is yet another object of the present invention to provide a massage drape that may be easily and securely attached to a person's body and may be easily shortened and lengthened once the person is on the massage table.

An additional object of the present invention is to provide a convenient and comfortable way to move from a face down to a face up position on the massage table.

These and other objects and advantages of the present invention will become readily apparent upon further review of the following drawings and specification.

BRIEF DESCRIPTION OF THE DRAWINGS

FIG. 6A is a view of the massage drape of FIG. 6 depicted the drape being elongated to expose the user's back.

DETAILED DESCRIPTION OF THE PREFERRED EMBODIMENT

Figure 1:
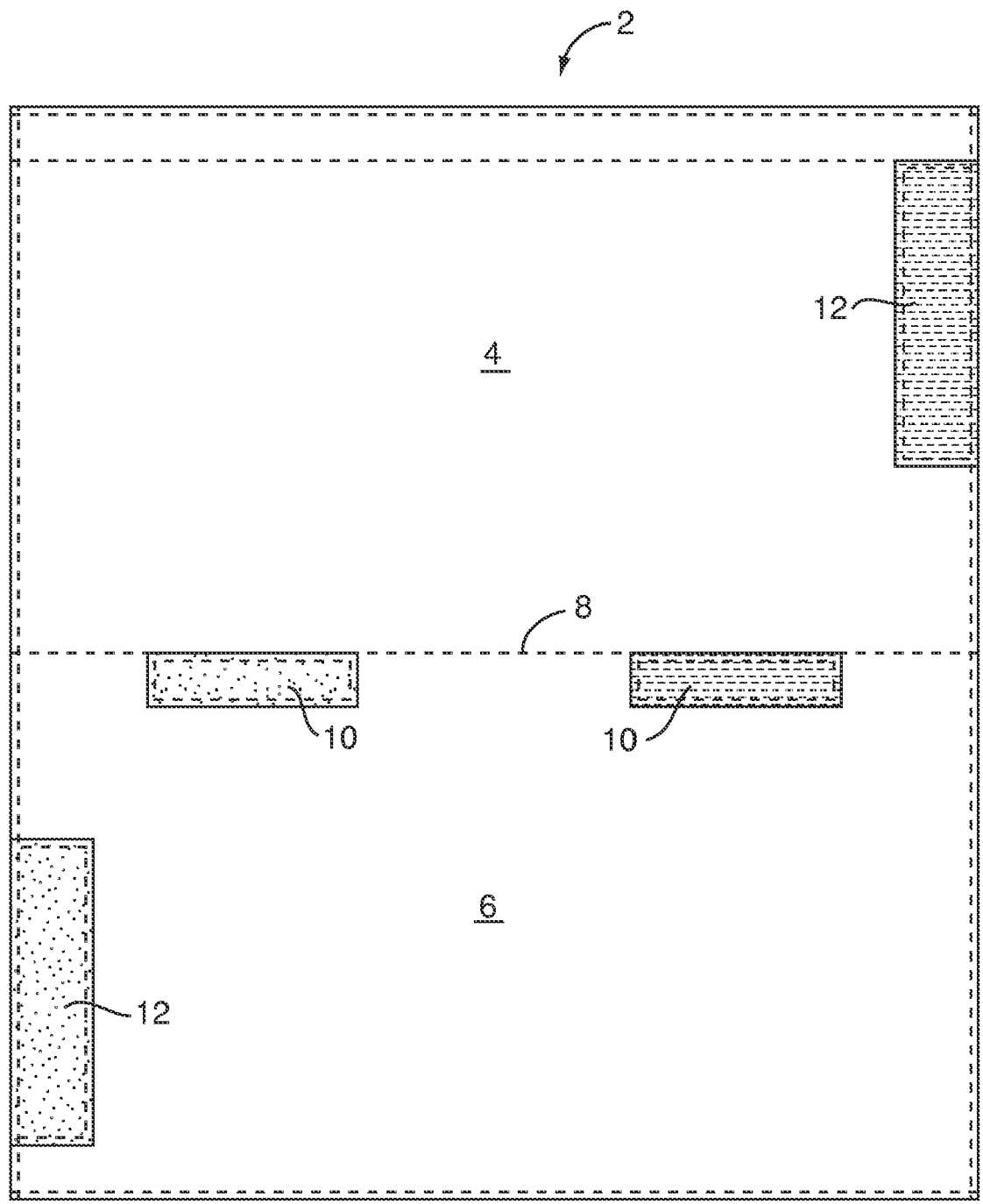
FIG. 1 is a plan view of the outer side of a massage drape made in accordance with the present invention illustrating the placement of hook and loop fasteners.

FIG. 1 depicts the outer side of a massage drape 2 of the present invention. The drape 2 has two sides, a first or outer side and a second or inner side, each of which have an upper portion 4 and a lower portion 6. The upper portion 4 and lower portions 6 are delineated by a crease or line 8 occurring at an approximate midpoint of the drape 2 creating upper and lower portions or halves 4, 6 of approximately equal size. Along the crease 8 are an outer hook and loop fastener 10, which, as described in greater detail below, may be employed to secure the drape 2 to a user under the user's arms or around the user's neck.

Additionally, the drape 2 includes hook and loop fasteners 12 positioned along opposite edges of the upper and lower portions 4, 6 of the drape 2. These allow the entire length of a folded drape 2 to be securely closed. The process of securing the drape 2 is described in greater detail below.

Preferably, the drape is manufactured from a sheet or sheet material. As will be appreciated, the sheet may be manufactured a variety of materials but is preferably a cotton fabric or a fabric containing a blend thereof. Other materials such as synthetic fabrics may be used as well. The preferred dimensions of an extended or unfolded drape are 94 inches by 66 inches. While other sizes may be employed, the above-referenced dimensions have been found to fit most people and provide sufficient coverage and comfort.

Additionally, as will be appreciated, other fasteners may be employed to secure the drape 2 to a user's body. Hook and loop fasteners, however, are preferred as they may be easily and quickly disengaged. In a preferred embodiment, the hook and loop fasteners 10 are 2 inches by 15 inches. Additionally, the fasteners 12 are 2 inches by 25 inches. As will be appreciated however, other sizes of hook and loop fasteners may be employed.

The crease 8 and outer hook and loop fasteners 10, 12 are important parts of the present invention. The crease permits the upper portion 4 of the drape 2 to be folded onto the lower portion 6 before being placed on the person's body, doubling the thickness of the material. This is important as it provides additional protection from nudity and warmth. The hook and loop fasteners 10, 12 allow the folded drape to be secured to the user's body.

Figure 2:
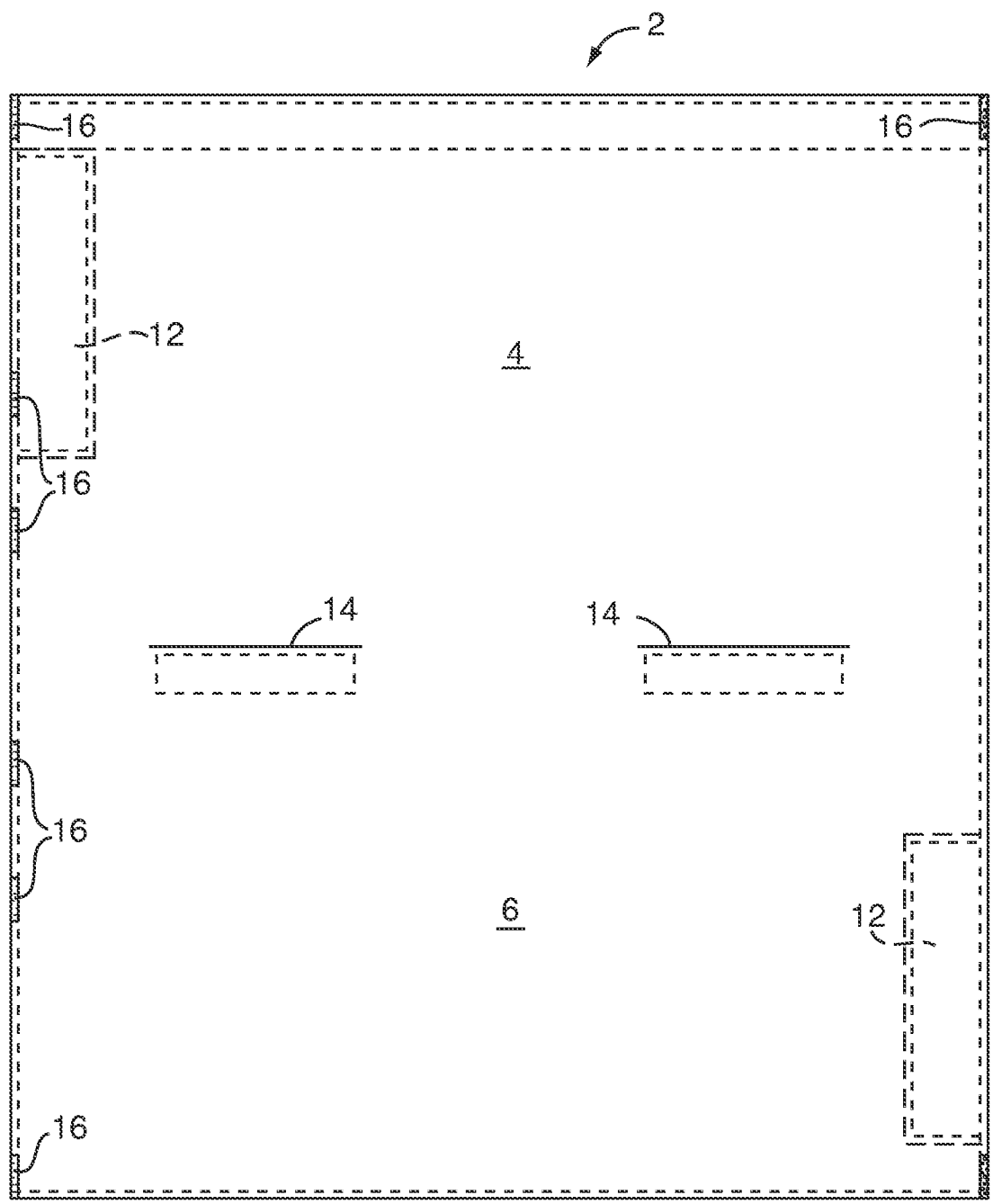
FIG. 2 is a plan view of the inner side of the massage drape of FIG. 1 depicting the placement of hook and loop fasteners and stitch creases.

Referring to FIG. 2, the inner surface or second side of the drape 2 has multiple hook and loop fasteners 16. The inner fasteners 16 are located along the perimeter or periphery of the inner surface of the drape 2. These inner fasteners 16 are an important aspect of the present invention as they are employed to secure the upper portion 4 of the drape 2 to the lower portion 6. While the preferred configuration of fasteners 16 is shown in FIG. 2, other configurations and types of fasteners may be employed. FIG. 2 also depicts the creases 14 formed by the hook and loop fasteners 10 that are sewn onto the outer surface of the drape 2 shown in FIG. 1.

In a preferred embodiment, the inner fasteners 16 are 2 inches by 1 centimeter. As will be appreciated, other sizes of hook and loop fasteners may be utilized.

Figure 3:
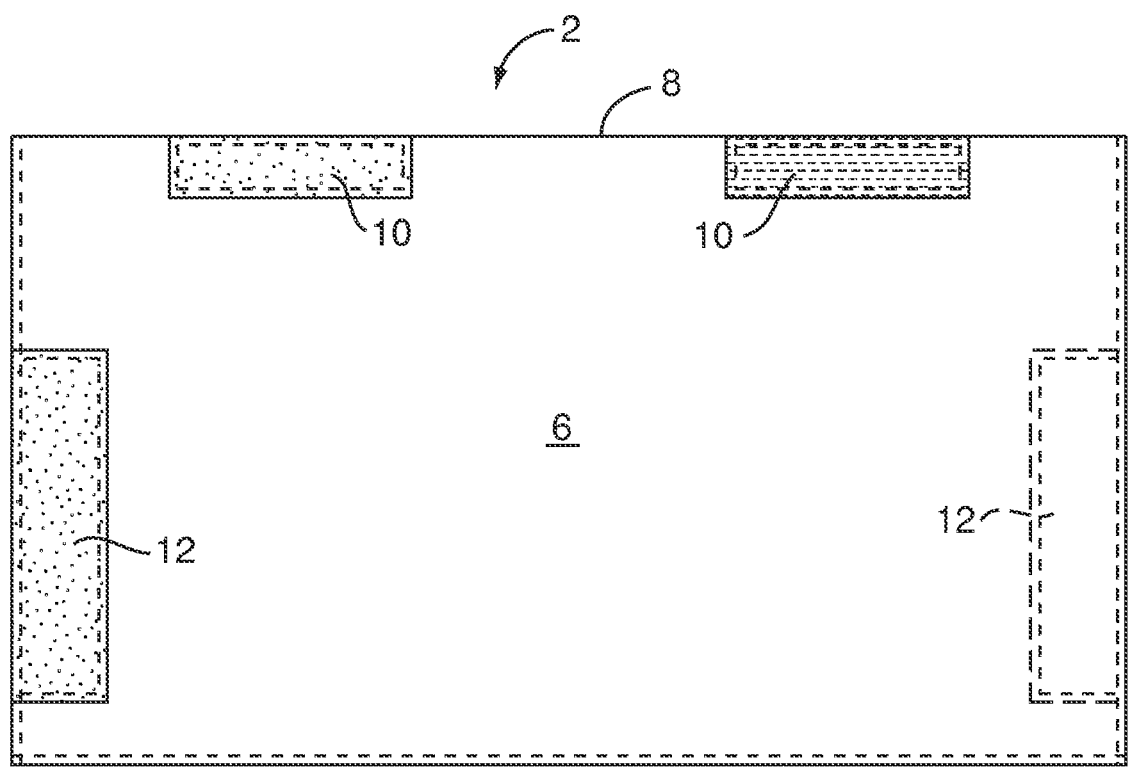
FIG. 3 is a plan view of the outer side of the massage drape of FIG. 1 wherein the drape is folded in half whereby the drape can be placed on a user's body.

Referring now to FIG. 3, the upper portion 4 (not shown) is folded onto the lower portion 6 to create a two-ply drape 2. As mentioned above the two-ply drape provides privacy and warmth above and beyond a conventional sheet. The upper portion 4 (not shown) is secured to the lower portion 6 through the hook and loop fasteners 16 (not shown) on the inner surface of the drape 2. Once the drape 2 has been folded and secured, it may be placed on a user.

Figure 4:
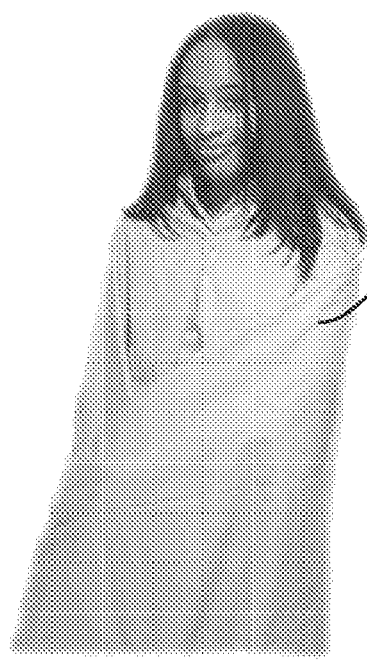
FIG. 4 is a view of the massage drape of FIG. 1 secured over a user's shoulder.
Figure 5:
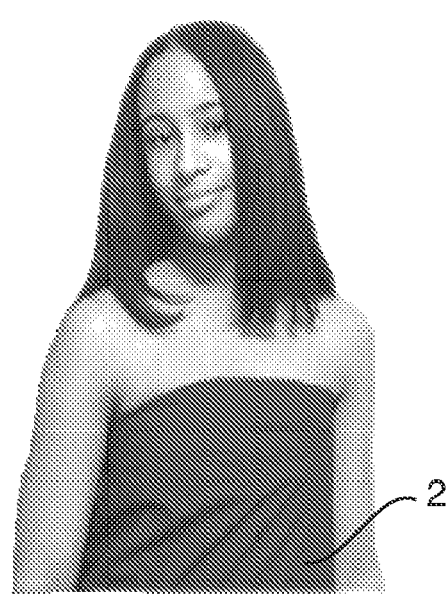
FIG. 5 is a view of the massage drape of FIG. 1 secured under a user's arms.

As shown in FIGS. 4 and 5, the drape 2 may be placed on and secured to a user several different ways. The drape 2 may be placed over a person's shoulders. In this configuration, the hook and loop fasteners 10 (not shown) are secured vertically down the person's chest. Additionally, the fasteners 12 are also secured so that the drape 2 is secured in a closed position from the top to bottom of a person's body. While both genders can use this configuration, males may find it ideal.

Turning now to FIG. 5, the drape 2 may also be secured to a person's body under their arms. In this configuration, the fasteners 10 (not shown) are secured horizontally across the user's chest. The fasteners 12 are not secured as they are unnecessary to close the drape 2. While both men and women may utilize this configuration, women may find it best suited given their anatomy.

Figure 6:
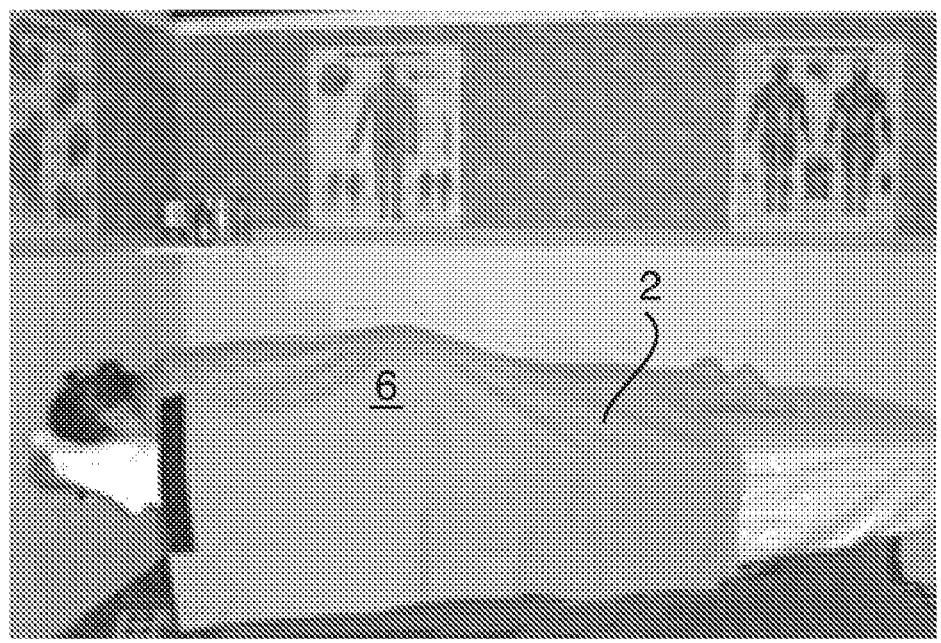
FIG. 6 is a view of the massage drape of FIG. 1 on a person positioned to receive a massage on a massage table.
Figure 7:
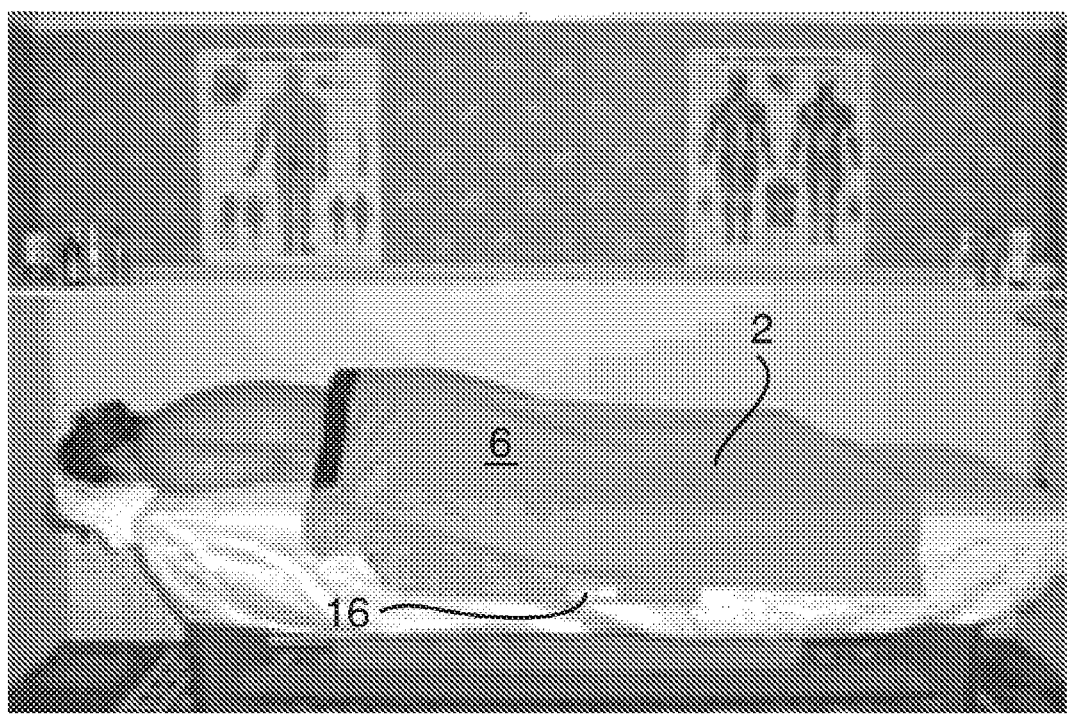

As mentioned above, the drape 2 is also used to selectively cover the user's body when they are receiving a massage. This is illustrated in FIGS. 6 and 6A. In FIG. 6, the user is in a face down position, and the drape 2 is covering the user's back. When the user's back and shoulders are to be exposed so that it may be massaged, the upper portion 6 of the drape 2 is pulled toward the user's feet thereby exposing the back area. As will be appreciated, the fastener 16 on the inner surface of the drape 2 must be unfastened in order to lower the upper portion 6 of the drape 2.

The ability to selectively shorten or lengthen the drape 2 by pulling on the upper portion or half 6 is an important aspect of the present invention. It is easy to utilize and it allows both sides of the drape 2 to be in contact with a portion of the user's body providing warmth. It is superior to a conventional drape or sheet which must be lifted and rotated 90 degrees from an initial position where the user is wearing the sheet to a position where the user's entire body is covered after he or she gets on the table. As will be appreciated, the lifting and rotating of the conventional sheet may completely expose the user's body and results in a single layer of material covering the body. The present invention eliminates this procedure.

Moreover, the drape 2 disclosed in the present application, is not limited to use for massages. The drape 2 may be used for multiple applications including to cover a person's body when they are on the beach or at home on a couch.

While the invention has been described with reference to the preferred embodiments, it will be understood by those skilled in the art that various obvious changes may be made, and equivalents may be substituted for elements thereof, without departing from the essential scope of the present invention. Therefore, it is intended that the invention not be limited to the particular embodiments disclosed, but that the invention includes all equivalent embodiments.

What is claimed is:

1. A massage drape for modesty and warmth, said drape comprising:

a substantially rectangular sheet having a length and width and a first side and a second side, each side having an upper portion and a lower portion;

a permanent seam extending along said entire width between the upper and lower portions of the sides facilitating the folding of the upper portion of said second side onto the lower portion of said second side to create a two-ply sheet, said seam dividing said upper and lower portions into approximately equal halves, wherein said two-ply sheet covers substantially all of a user's torso when a user is receiving a massage and said two-ply sheet may be adjusted to selectively reveal portions of a user's torso;

a plurality of inner fasteners located on the second side of the sheet allowing the upper and lower portions of the second side to be secured together after folding;

a first outer fastener on said lower portion of said first side; said first outer fastener positioned along the seam;

a second outer fastener located at opposite ends of both said upper portion and lower portion of said first side; and wherein upon folding and securing said upper and lower portions of said second side of said sheet using said inner fasteners, the sheet may be wrapped under a user's arms, such that said seam is aligned horizontally with a user's chest, and the first outer fastener may be closed securing the sheet to the user, the sheet may also be placed over a user's shoulders with said seam aligned vertically with a user's chest, and the first outer fastener may be closed to secure the sheet to the user's shoulders and the second outer fastener may be closed to prevent the sheet from opening and revealing a lower portion of the user's body, wherein whether said sheet is wrapped under a user's arms or over a user's shoulders, the user's chest and lower torso are covered for modesty.

2. The massage drape of claim 1 wherein the inner and outer fasteners are hook and loop closures.

3. The massage drape of claim 1 wherein the sheet is manufactured from a natural fiber.

4. The massage drape of claim 1 wherein the sheet is manufactured from a synthetic fiber or a blend of natural and synthetic fibers.

5. A massage drape for modesty and warmth, said drape comprising:

a substantially rectangular sheet having a length and a width, said sheet being defined by top, bottom and side peripheral edge portions, said top and bottom edge portions being parallel to one another and said side edge portions being parallel to one another and perpendicular to said top and bottom edge portions, said sheet also having corresponding first and second sides, each side having an upper portion and a lower portion;

a permanent seam extending along the entire width of said substantially rectangular sheet, said seam defining said upper and lower portions of the sheet and facilitating the folding of the upper portion of said second side onto the lower portion of said second side to create a two-ply sheet, said seam dividing said upper and lower portions into approximately equal halves, wherein said two-ply sheet covers substantially all of a user's torso when a user is receiving a massage and said two-ply sheet may be adjusted to selectively reveal portions of a user's torso;

a plurality of inner hook and loop fasteners located along the peripheral edge portions of the second side of the sheet allowing the upper and lower portions of the second side to be secured together after folding;

a first outer hook and loop fastener on said lower portion of said first side; said first outer hook and loop fastener positioned along the seam;

a second outer hook and loop fastener located adjacent opposite side edge portions and at opposite ends of both said upper portion and lower portion of said first side; and wherein upon folding and securing said upper and lower portions of said second side of said sheet using said inner fasteners, the sheet may be wrapped under a user's arms, such that said seam is aligned horizontally with a user's chest, and the first outer hook and loop fastener may be closed securing the sheet to the user, the sheet may also be placed over a user's shoulders with said seam aligned vertically with a user's chest, and the first outer hook and loop fastener may be closed to secure the sheet to the user's shoulders and the second outer hook and loop fastener may be closed to prevent the sheet from opening and revealing a lower portion of the user's body, wherein whether said sheet is wrapped under a user's arms or over a user's shoulders, the user's chest and lower torso are covered for modesty.

6. The massage drape of claim 5 wherein the sheet is manufactured from a natural fiber.

7. The massage drape of claim 5 wherein the sheet is manufactured from a synthetic fiber or a blend of natural and synthetic fibers.

* * * * *